United States Patent [19]

Markwell et al.

[11] Patent Number: 4,716,160
[45] Date of Patent: Dec. 29, 1987

[54] CERTAIN 7-AMINO-PYRAZOLO[4,3-B]PYRIDINES USEFUL IN TREATING INFLAMMATORY AND ALLERGIC DISORDERS

[75] Inventors: Roger E. Markwell, Great Dunmow; Robert W. Ward, Old Harlow; Carol R. de Mello, North Mymms, all of England

[73] Assignee: Beecham Group p.l.c., Brentford, England

[21] Appl. No.: 856,454

[22] Filed: Apr. 25, 1986

[30] Foreign Application Priority Data

Apr. 27, 1985 [GB] United Kingdom ............ 8510774
Mar. 20, 1986 [GB] United Kingdom ............ 8606885

[51] Int. Cl.$^4$ .................. A61K 31/44; C07D 471/04
[52] U.S. Cl. ........................... 514/212; 514/293; 514/303; 540/597; 546/82; 546/119; 546/120
[58] Field of Search ............ 546/82, 119, 120; 514/293, 303, 212; 540/597

[56] References Cited

U.S. PATENT DOCUMENTS 4,559,348 12/1985 Hurst et al. ............ 514/303
4,576,952 3/1986 Hurst et al. ............ 546/119

FOREIGN PATENT DOCUMENTS 0152910 2/1985 European Pat. Off.
0154220 9/1985 European Pat. Off.

OTHER PUBLICATIONS

P. Sykes, "A Guidebook to Mechanism in Organic Chemistry", Longmans, Green and Co., London (1965) pp. 128–129.
E. Ajello, "New Synthesis of Condensed Heterocycles from Isoxazole Derivatives. II. Pyrazolo [4,3-b]-pyridine", *J. Heterocyclic Chem.*, 8, pp. 1035–1037 (1971).

*Primary Examiner*—Richard A. Schwartz
*Assistant Examiner*—Bernard I. Dentz
*Attorney, Agent, or Firm*—James F. Haley, Jr.; Teresa L. Solomon

[57] ABSTRACT

Compounds of formula (I)

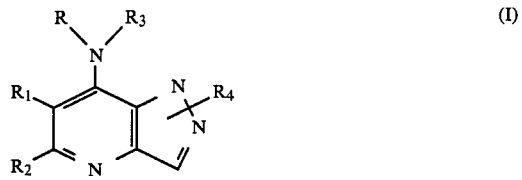

wherein:
R is hydrogen or $C_{1-6}$ alkyl;
$R_1$ and $R_2$ are both hydrogen; or
$R_1$ is hydrogen, $C_{1-6}$ alkyl; and $R_2$ is CN; $CR_5R_6Y$ where $R_5$ and $R_6$ are independently selected from hydrogen and $C_{1-4}$ alkyl and Y is selected from hydrogen, $OR_7$ or $SR_7$ where $R_7$ is hydrogen, $C_{1-4}$ alkyl or $C_{2-4}$ alkanoyl, and $NR_8R_9$ where $R_8$ and $R_9$ are independently hydrogen, $C_{1-4}$ alkyl, $C_{2-4}$ alkenyl or $C_{2-4}$ alkanoyl or together are $C_{4-6}$ polymethylene, or $COR_{10}$ where $R_{10}$ is OH or $C_{1-4}$ alkyl, or $COR_{10}$ is a pharmaceutically acceptable ester or amide; or
$R_2$ is hydrogen, $C_{1-6}$ alkyl, or phenyl optionally substituted by halogen, $CF_3$, $C_{1-4}$ alkoxy or $C_{1-4}$ alkyl; and $R_1$ is CN, $CR_5R_6Y$ or $COR_{10}$ as defined for $R_2$ above; or
$R_1$ and $R_2$ together form $C_3$–$C_6$ polymethylene optionally substituted by $C_1$–$C_4$ alkyl;
$R_3$ a mono- or fused bi-cyclic heteroaryl group having up to ten atoms in the aromatic ring(s), not more than two of which are selected from nitrogen, oxygen or sulphur, other than those containing basic nitrogen, optionally substituted by one or two substituents selected from halogen, $CF_3$, $C_{1-4}$ alkoxy, $C_{1-4}$ alkyl, hydroxy, nitro, cyano, $C_{2-10}$ acyloxy, $NR_{11} R_{12}$ wherein $R_{11}$ and $R_{12}$ are independently selected from hydrogen, $C_{1-6}$ alkyl, $C_{2-7}$ alkanoyl or $C_{1-6}$ alkylsulphonyl; or $COR_{13}$ wherein $R_{13}$ is hydroxy, $C_{1-6}$ alkoxy or $NR_{14} R_{15}$ wherein $R_{15}$ and $R_{14}$ are independently selected from hydrogen or $C_{1-6}$ alkyl; and
$R_4$ is hydrogen, or $C_{1-4}$ alkyl, or benzyl optionally substituted in the phenyl ring by one or more of halogen, $CF_3$, $C_{1-4}$ alkyl, and is attached at nitrogen atom 1 or 2; show anti-inflammatory and anti-allergy activity.

8 Claims, No Drawings

CERTAIN 7-AMINO-PYRAZOLO[4,3-B]PYRIDINES USEFUL IN TREATING INFLAMMATORY AND ALLERGIC DISORDERS

The present invention relates to pyrazolopyridines having useful pharmacological activity, to a process for their preparation and to their use as pharmaceuticals.

European Patent Publication No. 119774 discloses a group of pyrazolopyridine derivatives which are described as of potential use as anti-inflammatories.

A structurally distinct group of pyrazolopyridine derivatives has now been discovered which compounds have anti-inflammatory (such as topical anti-inflammatory and anti-rheumatic) and/or anti-allergy activity.

Accordingly, the present invention provides a compound of the formula (I) or a salt or solvate thereof:

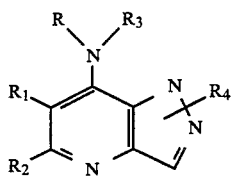

(I)

wherein:

R is hydrogen or $C_{1-6}$ alkyl;
$R_1$ and $R_2$ are both hydrogen; or
$R_1$ is hydrogen, $C_{1-6}$ alkyl or phenyl; and $R_2$ is CN; $CR_5R_6Y$ where $R_5$ and $R_6$ are independently selected from hydrogen and $C_{1-4}$ alkyl and Y is selected from hydrogen, $OR_7$ or $SR_7$ where $R_7$ is hydrogen, $C_{1-4}$ alkyl or $C_{2-4}$ alkanoyl, and $NR_8R_9$ where $R_8$ and $R_9$ are independently hydrogen, $C_{1-4}$ alkyl, $C_{2-4}$ alkenyl or $C_{2-4}$ alkanoyl or together are $C_{4-6}$ polymethylene; or $COR_{10}$ where $R_{10}$ is OH or $C_{1-4}$ alkyl, or $COR_{10}$ is a pharmaceutically acceptable ester or amide. or
$R_2$ is hydrogen, $C_{1-6}$ alkyl, or phenyl optionally substituted by halogen, $CF_3$, $C_{1-4}$ alkoxy or $C_{1-4}$ alkyl; and $R_1$ is CN, $CR_5R_6Y$ or $COR_{10}$ as defined for $R_2$ above; or
$R_1$ and $R_2$ together form $C_3$-$C_6$ polymethylene optionally substituted by $C_1$-$C_4$ alkyl;
$R_3$ is a mono- or fused bi-cyclic heteroaryl group having up to ten atoms in the aromatic ring(s), not more than two of which are selected from nitrogen, oxygen or sulphur, other than those containing basic nitrogen, optionally substituted by one or two substituents selected from halogen, $CF_3$, $C_{1-4}$ alkoxy, $C_{1-4}$ alkyl, hydroxy, nitro, cyano, $C_{2-10}$ acyloxy, $NR_{11}$ $R_{12}$ wherein $R_{11}$ and $R_{12}$ are independently selected from hydrogen, $C_{1-6}$ alkyl, $C_{2-7}$ alkanoyl or $C_{1-6}$ alkylsulphonyl; or $COR_{13}$ wherein $R_{13}$ is hydroxy, $C_{1-6}$ alkoxy or $NR_{14}$ $R_{15}$ wherein $R_{15}$ and $R_{14}$ are independently selected from hydrogen or $C_{1-6}$ alkyl; and
$R_4$ is hydrogen, or $C_{1-4}$ alkyl, or benzyl optionally substituted in the phenyl ring by one or more of halogen, $CF_3$, $C_{1-4}$ alkyl, and is attached at nitrogen atom 1 or 2.

Suitable values for R include hydrogen, methyl, ethyl, n- and iso-propyl, preferably hydrogen.

Suitable values for $R_1$ and $R_2$ when $COR_{10}$ include $COR_{10}{}^1$ wherein $R_{10}{}^1$ is hydroxy, $C_{1-6}$ alkoxy, $C_{2-6}$ alkenyloxy, phenoxy or benzyloxy wherein the phenyl/benzyl moiety is optionally substituted by one or two of halogen, $CF_3$, $C_{1-4}$ alkoxy and $C_{1-4}$ alkyl; or $R_{10}{}^1$ is $NR_{16}R_{17}$ wherein $R_{16}$ and $R_{17}$ are independently hydrogen, $C_{2-6}$ alkyl, $C_{2-6}$ alkenyl, benzyl or phenyl optionally substituted as described above.

Examples of $R_{10}{}^1$ include hydroxy, methoxy, ethoxy, n- or iso- propoxy, amino, methylamino, dimethylamino, anilino and allylamino.

Suitable values for $R_1$ and $R_2$ when other than $COR_{10}$, include hydrogen, methyl, ethyl, n- and iso-propyl and phenyl, aminomethyl optionally N- substituted and acetamidomethyl, or $R_1$ and $R_2$ together may be $C_{3-4}$ polymethylene.

Often $R_1$ is hydrogen or $COR_{10}$ and $R_2$ is hydrogen or methyl.

Suitable values for $R_3$ include furyl, thienyl, pyrryl, benzofuranyl, benzothienyl and indolyl optionally substituted by one or two chloro, bromo, methoxy, ethoxy, n- and iso-propoxy, methyl, ethyl, n- and iso-propyl, n-, iso-, sec- and tert-butyl, hydroxy, nitro, cyano, acetoxy, propionyloxy, benzyloxy, $NR_{11}{}^1R_{12}{}^1$ wherein $R_{11}{}^1$ and $R_{12}{}^1$ are independently selected from hydrogen, methyl, ethyl, n- and iso-propyl, acetyl and propionyl; $COR_{13}{}^1$ wherein $R_{13}{}^1$ is hydroxy, methoxy, ethoxy or $NR_{14}{}^1R_{15}{}^1$ wherein $R_{14}{}^1$ and $R_{15}{}^1$ are independently selected from hydrogen, methyl, n- and iso-propyl.

Preferably $R_3$ is 2- or 3- thienyl optionally substituted as defined above.

Suitable values for $R_4$ include hydrogen, methyl, ethyl, n- and iso-propyl and benzyl. More suitably $R_4$ is hydrogen or 2-methyl. Favourably $R_4$ is hydrogen.

It will be appreciated that when $R_4$ is hydrogen the compounds of formula (I) exist as tautomers, i.e. the $R_4$ hydrogen atom is labile. The compounds wherein $R_4$ is hydrogen are therefore of formulae (IIa) and (IIb).

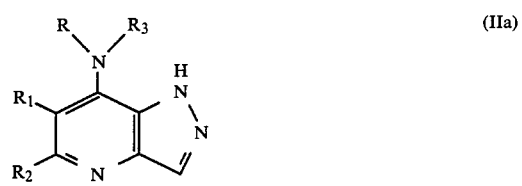

(IIa)

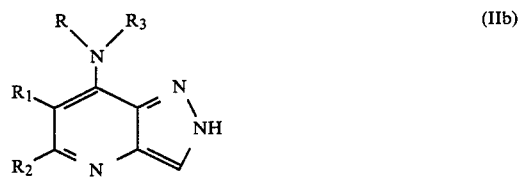

(IIb)

The compounds of the formula (I) can form acid addition salts with acids, such as the conventional pharmaceutically acceptable acids, for example hydrochloric, hydrobromic, phosphoric, acetic, fumaric, salicylic, citric, lactic, mandelic, tartaric and methanesulphonic. Such compounds form part of the present invention, as do solvates, for example hydrates, of the compounds of formula (I) or salts thereof.

There is a group of compounds within formula (I) of formula (III):

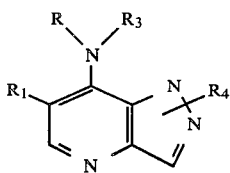

A further group of compounds within formula (I) is of formula (IV):

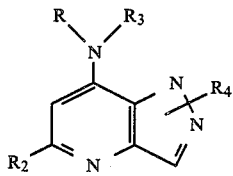

Another group of compounds within formula (I) is of formula (V):

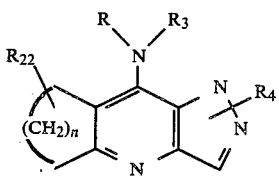

in which n is 3 to 5 and $R_{22}$ is hydrogen or $C_1$–$C_4$ alkyl.

In formula (III), (IV) and (V), R, $R_1$, $R_2$, $R_3$, $R_4$ and suitable and preferred values for these variables, are as described in formula (I).

The present invention also provides a process for the preparation of a compound of formula (I) or a salt or solvate thereof, which process comprises the reaction of a compound of formula (VI):

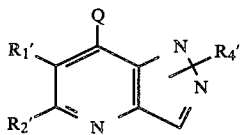

wherein Q is a leaving group and $R_1'$, $R_2'$ and $R_4'$ are $R_1$, $R_2$ and $R_4$ or groups or atoms convertible thereto, with a compound of formula (VII):

HNR'$R_3'$      (VII)

wherein R' is R as defined for formula (1) or a group or atom convertible thereto, and $R_3'$ is $R_3$ as defined for formula (I) or a group or atom convertible thereto, to obtain a compound of formula (Ia)

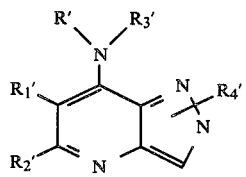

and then performing one or more of the following steps:
(a) when one or more of R', $R_1'$, $R_2'$, $R_3'$ or $R_4'$ are not R, $R_1$, $R_2$, $R_3$ or $R_4$ respectively, converting said one or more substituents to R, $R_1$, $R_2$, $R_3$ or $R_4$ to obtain a compound of formula (I);
(b) when R', $R_1'$, $R_2'$, $R_3'$ and $R_4'$ are R, $R_1$, $R_2$, $R_3$ and $R_4$ converting one or more of $R_1$, $R_2$, $R_3$ and $R_4$ to another $R_1$, $R_2$, $R_3$ or $R_4$ to obtain a compound of formula (I);
(c) forming a salt and/or solvate of the obtained compound of formula (I).

It will be appreciated that a compound of formula (Ia), or another compound of formula (I), may be converted to compound of formula (I) by interconversion of suitable substituents. Thus certain compounds of formula (I) are useful intermediates in forming other compounds of the present invention.

Salts or solvates of the compounds of formula (I) are preferably pharmaceutically acceptable, but those which are not pharmaceutically acceptable may be useful as intermediates in the production of pharmaceutically acceptable salts or solvates. Accordingly such salts or solvates also form part of this invention.

Suitable leaving groups Q include halogens such as chloro and bromo, preferably chloro.

The reaction may be carried out under conventional conditions for nucleophilic aromatic displacements, at elevated temperatures using excess of reagent as solvent or in an inert solvent such as toluene, ethanol, dimethylformamide, dimethylsulphoxide, dioxan or water.

Advantageously, $R_3'$ is a carboxylated heterocycle $R_3$ which decarboxylates in situ to $R_3$ when the compound of formula (VI) is reacted with the compound of formula (VII). In this case the reaction preferably takes place in the presence of acetic acid in addition to any inert solvent that is used.

Conversion of an R hydrogen to an R $C_{1-6}$ alkyl group may be carried out by conventional amine alkylation (with protection of $R_4$ if hydrogen), or, if appropriate, acylation (e.g. formylation) followed by reduction.

An $R_{10}$ hydroxy group in $R_1$ or $R_2$ may be converted to an $R_{10}$ alkoxy group by conventional esterification procedures and an $R_{10}$ hydroxy group may be converted to an amino group by condensation with an amine and in the presence of a dehydrating agent, such as dicyclohexylcarbodiimide.

A $COR_{10}$ group when amide can be converted to a $COR_{10}$ ester group by conventional hydrolysis/esterification in ethanolic HCl. One $COR_{10}$ ester group may be converted to another $COR_{10}$ ester by conventional transesterification procedures. It will be appreciated that when $R_2$ is an ester group, reaction of the compound of formula (VI) with the compound of formula (VII) may also substitute $R_{10}$, in which case subsequent conversion of $R_{10}$ is necessary as described above.

$R_1'$ or $R_2'$ may be methyl, in which case it may be converted to a $CO_2H$ group by conventional oxidation with an oxidising agent such as potassium permanganate. This conversion is preferably, however, carried out on the intermediate of formula (VI) or at an earlier stage.

Compounds of the formula (I) wherein $R_1/R_2$ is COOH may be converted to compounds of the formula (I) wherein $R_1/R_2$ is hydrogen by conventional decarboxylation methods such as heating in a high boiling inert solvent e.g. Dowtherm.

To obtain a compound of formula (I) in which $R_1$ is hydrogen and the compound of formula (VII) is a relatively unreactive amine, it is advantageous that $R_1'$ in formula (V) is alkoxycarbonyl, most preferably ethoxycarbonyl. $R_1'$ alkoxycarbonyl may then be converted to $R_1$ hydrogen by conventional base hydrolysis followed by decarboxylation.

Conversions of substituents on $R_3$ are generally known in the art of aromatic chemistry. Examples of such conversions are as follows:

(a) an hydroxy group may be converted to acyloxy by conventional acylation procedures, preferably using the acid anhydride in trifluoroacetic acid at elevated temperature;

(b) a cyano group may be converted to carboxy by base catalysed hydrolysis; preferably using sodium hydroxide in ethanol followed by neutralisation with acid.

(c) an alkoxycarbonyl group may be converted to amido or substituted amido by heating with the appropriate amine;

(d) a nitro group may be converted to an amino group by reduction, preferably by catalytic reduction using palladium on charcoal;

(e) an amino group may be converted to an alkylamino or acylamino group by conventional amine acylation or alkylation; the acylation is preferably carried out using an acid anhydride and the alkylation using the alkyl halide;

(f) an amino group may be converted to an alkylsulphonyl group by reaction with the appropriate alkylsulphonyl chloride, preferably using an acid acceptor such as triethylamine in an inert solvent such as dichloromethane.

(g) A carboxyl group may be converted to hydrogen by conventional decarboxylation.

An $R_4$ hydrogen atom may be converted to an $R_4$ $C_{1-6}$ alkyl group by conventional alkylation procedures.

It will be appreciated that these conversions may take place in any desired or necessary order. Conversions involving amine substitution may also substitute an $R_4$ hydrogen which therefore may need to be protected using an amine protecting group.

Pharmaceutically acceptable salts of the compounds of formula (I) may be formed conventionally by reaction with the appropriate acid.

Compounds of the formula (VI) are either known compounds or can be prepared by analogy with processes for preparing structurally similar known compounds.

For example, compounds of the formula (VI) wherein Q is chloro may be prepared by the phosphorus oxychloride chlorination of a compound of formula (VIII):

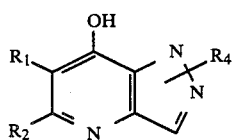

(VIII)

Compounds of the formula (VIII) may be prepared as described in J. Chem. Soc. Perkin Trans. I, 1976 (5), 507 or by analogous methods thereto.

It will be appreciated that the compounds of formula (VIII) wherein $R_4$ is hydrogen exist in the predominant tautomeric form of formula (VIIIa):

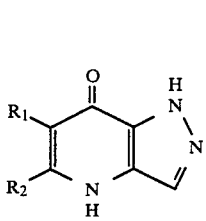

(VIIIa)

In a further aspect the invention provides a pharmaceutical composition which comprises a compound of formula (I) or a pharmaceutically acceptable salt or solvate thereof and a pharmaceutically acceptable carrier.

The compositions may be adapted for administration via the topical, oral, vaginal, rectal or injection routes. The compositions of this invention may be prepared by admixture of the active agent with the carrier and optionally diluents, binder, fillers, disintegrants, flavouring agents, colouring agents, lubricants, preservatives in conventional manner. These conventional excipients may be employed in conventional manner, for example as in the preparation of compositions of ketoprofen, indomethacin, naproxen, acetylsalicylic acid or other anti-inflammatory agents.

The compounds of the invention have topical anti-inflammatory activity and therefore a compound of formula (I) will normally be dispersed in a cream, lotion, gel, gel stick, ointment, douche, wash, spray, or aerosol vehicle for topical administration to the skin or mucosal membranes.

Cream, lotion, gel, gel stick, ointment, douche, wash, spray, or aerosol formulations that may be used for compounds of the formula (I) are conventional formulations well known in the art, for example, as described in standard text books of pharmaceutics and cosmetics, such as Harry's Cosmeticology published by Leonard Hill Books, Remington's Pharmaceutical Sciences published by Mack Publishing Co., and the British and US Pharmacopoeias. A standard emulsifying ointment base or glycerol or anhydrous polyethylene glycol are simple examples of suitable vehicles. Aqueous solutions or dispersions may be used as, for example, vaginal douches or washes for mouth or throat.

Examples of oils suitable for inclusion in a standard emulsifying ointment base include mineral oils, vegetable oils, synthetic fatty acid esters, fatty alcohols, lanolin and its derivatives.

These compositions will normally include a suitable emulsifier. The composition can range from liquid through semi-liquid to gel types according to the type of emulsion and quantity of any thickening agent which may be present. Examples of emulsifiers include polyhydric alcohol esters such as sorbitan monostearate, fatty acid esters such as glyceryl monostearate, and polyester derivatives of fatty acids or fatty alcohols.

The compositions may also contain anti-oxidants and other conventional ingredients such as preservatives, perfumes and alcohol. Advantageously, a penetrating agent such as AZONE may also be included.

The compositions for topical treatment may also contain other therapeutic agents such as anti-infective and/or anti-viral agents. Suitable anti-infective agents include the topically applicable antibacterial, anti-yeast, anti-fungal and anti-herpes agents.

These compositions may be used in the topical treatment of atopic and contact dermatitis, psoriasis, acne, eczema and other inflammatory dermatoses and inflammatory conditions such as lesions of eyes, ears, nose, throat, vagina and rectum, particularly mucosal membranes. Treatment of inflammation of the skin and mucosal membranes may, however, also be carried out utilising an oral composition of the invention, as hereinbefore described.

It will be appreciated that the amount of compound of the formula (I) used will depend on a number of factors such as the nature and severity of the disorder being treated, and the specific compound being used. However, by way of illustration it is believed that effective therapy can be achieved using roughly similar amounts of the compounds of formula (I) as would be used of hydrocortisone. A typical formulation will suitably contain 0.1 to 20%, more suitably 0.5 to 5% of the compound of formula (I).

A composition of this invention is useful in the treatment of rheumatism and arthritis and in the treatment of pain and other inflammatory conditions and also in the treatment of the prophylaxis of bronchial asthma, rhinitis, hay fever and allergic eczema. Suitably the oral compositions of this invention will be in the form of a unit dose such as a tablet, capsule or reconstitutable powder in a sachet. Such unit doses will generally contain from 10 mg to 1000 mg and more suitably will contain from about 30 mg to 500 mg for example 50 mg to 250 mg of active agent, for example about 50, 100, 150, 200, 250, 300, 350, 400, 450 or 500 mg. These compositions may be administered once or more times a day, for example 2,3 or 4 times daily, so that the total daily dose for a 70 kg adult will usually be in the range of 20 to 3000 mg and more usually in the range 40 to 1000 mg. Alternatively the unit dose may contain from 2–20 mg of active agent and may be administered in multiples if desired to give the preceeding daily dose.

For use in the treatment of prophylaxis of allergic disorders, in any of the preceding formulations, a suitable dosage unit may contain 0.01 to 500 mg of active ingredient, more suitably 1 to 500 mg for use via the oral route, 0.01 to 10 mg via inhalation, which is preferred. The effective dose of compound depends on the particular compound employed, the condition of the patient and the frequency and route of administration, but in general is in the range of from 0.001 mg/day to 100 mg/day per kilogram of the patient's body weight.

No adverse toxicological effects are indicated at any of the aforementioned dosage ranges.

Where appropriate, small amounts of other antiasthmatics and bronchodilators, for example sympathomimetic amines such as isoprenaline, isoetharine, salbutamol, phenylephrine and ephedrine; xanthine derivatives such as theophylline and aminophylline and corticosteroids such as prednisolone and adrenal stimulants such as ACTH may be included.

A favoured form of oral composition of this invention is a tablet containing the active agent. The active agent may be in the form of a recompressed granulate of the active ingredient in intimate mixture with a lubricant such as magnesium stearate, a filler such as microcrystalline cellulose and a disintegrant such as sodium starch glycollate.

A particular composition of the invention for inflammatory diseases is a hard gelatin capsule containing the required amount of a compound of the invention in the form of a powder or granulate in intimate mixture with a lubricant, such as magnesium stearate, a filler, such as microcrystalline cellulose, and a disintegrant, such as sodium starch glycollate.

Preparations especially suitable for administration to the respiratory tract include, for example, a snuff, an aerosol, a solution for a nebulizer, or a microfine powder for insufflation, alone or in combination with an inert carrier such as lactose. In such a case the particles of active compound suitably have diameters of less than 50 microns, preferably less than 10 microns.

For parenteral administration, fluid unit dosage forms are prepared utilising a compound of the formula (I) or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. Parenteral suspensions are prepared in substantially the same manner, except that the compound is suspended in the vehicle instead of being dissolved and sterilised by exposure to ethylene oxide before suspension in a sterile vehicle. Advantageously, a surfactant or wetting agent is included in the composition to facilitate uniform distribution of the compound.

The invention further provides a method of treatment or prophylaxis of inflammatory and/or allergic conditions in mammals including man which comprises the administration of a compound of formula (I) or a pharmaceutically acceptable salt or solvate thereof to the sufferer.

The invention also provides a compound of formula (I) or a pharmaceutically acceptable salt or solvate thereof as an active therapeutic substance for use in treating disorders in mammals, and in particular inflammatory and/or allergic conditions.

The invention also provides the use of a compound of formula (I) or a pharmaceutically salt or solvate thereof in the manufacture of a medicament for use in treating inflammatory and/or allergic conditions.

Mammals which may be thus treated include humans and domestic animals such as dogs, cats or horses.

Most suitably the medicament will be administered orally as 1, 3 or 4 doses per day at the dose level previously indicated.

The following Description, Examples and Pharmacological Data illustrate intermediates for the compounds of this invention, the compounds of this invention and the process for preparing them, and their pharmacological activity.

Description 1

Ethyl 7-chloro-1H-pyrazolo[4,3-b]pyridine-6-carboxylate

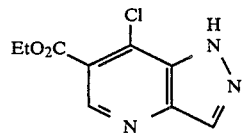

A solution of ethyl 4,7-dihydro-7-oxo-1H-pyrazolo[4,3-b]pyridine-6-carboxylate[1] in phosphorus oxychloride was heated under reflux for 45 min. After removing excess reagent in vacuo, the residue was made basic with saturated sodium hydrogen carbonate solution. The precipitated solid was washed with water, then extracted with ethyl acetate to give the crude title compound.

1. H. E. Foster and J. Hurst, J. Chem. Soc., Perkin Trans. 1, 1976, 507

δ(DMSO d6): 1.4 (3H, t, J=7 Hz), 4.3 (2H, q, J=7 Hz), 8.4 (1H, s), 8.8 (1H, s).

A much improved yield (67%) of the title compound was obtained by maintaining the reaction mixture at 70°-80° C. rather than at reflux temperature.

EXAMPLE 1

Ethyl 7-thienylamino-1H-pyrazolo[4,3-b]pyridine-6-carboxylate (E1)

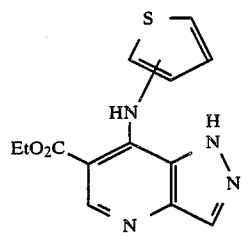

Ethyl 7-chloro-1H-pyrazolo[4,3-b]pyridine-6-carboxylate (4.5 g 0.02 mole) and aminothiophene (2.0 g) [prepared from 2-nitrothiophene (supplied by Aldrich and shown by nmr to contain 15% of 3-nitrothiophene) by reduction using either $H_2$; 10% Pd/C or stannous chloride] were stirred together under nitrogen for 24 hours. The ethanol was removed under reduced pressure. The resulting brown oil was purified by column chromatography on silica eluting with 5% methanol/ether to give the title compound as a beige solid (0.600 g), mp 188°-190° C.

δ(CDCl$_3$): 1.45 (3H, t, J=7 Hz), 4.4 (2H, q, J=7 Hz), 7.1-7.6 (3H, overlapping m), 8.18 (1H, s), 9.05 (1H, s).

Found: M+ 288.0686.

$C_{13}H_{12}N_4O_2S$ requires 288.0680.

EXAMPLE 2

7-Thienylamino-1H-pyrazolo[4,3-b]pyridine (E2)

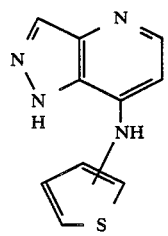

Ethyl 7-thienylamino-1H-pyrazolo[4,3-b]pyridine-6-carboxylate (0.600 g) was converted to the corresponding acid by heating under reflux with a 2% sodium hydroxide solution in ethanol (50 ml). The ethanol was removed under reduced pressure and the residue diluted with water (5 ml) and acidified to pH5 with dilute hydrochloric acid. The resulting acid was filtered off and dried, mp 255°-259° C.

The above acid was dissolved in Dowtherm A (20 ml) and heated under reflux under nitrogen for 30 min. The reaction mixture was cooled and diluted with a large volume of 60°-80° C. petroleum ether. The resulting solid was filtered off. This was chromatographed on silica eluting with 5% methanol/chloroform to give the title compound as a light grey solid as a 4:1 mixture of isomers (2-thienyl:3-thienyl), mp 216°-220° C.

δ(CDCl$_3$): 6.78 (1H, d, J=5 Hz), 6.8-7.25 and 7.48-7.55 (total 3H, m), 8.18 (1H, s), 8.20-8.3 (1H, 2 overlapping doublets).

Found: M+ 216.0471.

$C_{10}H_8N_4S$ requires 216.0470.

EXAMPLE 3

Ethyl 7-(3-thienylamino)-1H-pyrazolo[4,3-b]pyridine-6-carboxylate (E3)

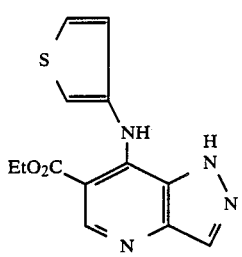

Methyl 3-aminothiophene-2-carboxylate (8.0g; 0.05 mole) was added to a solution of sodium hydroxide (2.2 g; 0.055 mole) in water (50 ml) and the mixture heated under reflux for 3 hours. Evaporation in vacuo gave an off-white powder (10 g) which was suspended in dry toluene (100 ml) containing a solution of ethyl 7-chloro-1H-pyrazolo[4,3-b]pyridine-6-carboxylate (3.0 g) in ethanol (30 ml).

Glacial acetic acid (12 ml) was added in one portion. The reaction mixture was left stirring at room temperature for 48 hours. The solvents were removed under reduced pressure and sufficient 10% sodium carbonate solution added to the slurry to give pH 8. The resulting solid was collected, dried and recrystallised from ether/ethyl acetate to give the title compound (2.4 g), m.p. 174°-175° C.

δ(CDCl$_3$): 1.45 (3H, t, J=7 Hz), 4.4 (2H, q, J=7 Hz), 6.95-7.45 (3H, m), 8.05 (1H, s), 8.99 (1H, s).

EXAMPLE 4

7-(3-Thienylamino)-1H-pyrazolo[4,3-b]pyridine (E4)

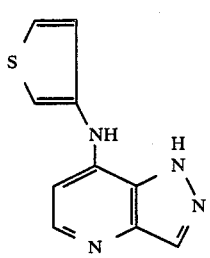

The above compound was prepared in an analogous manner to the preparation of Example 2 to give (E4) as a light beige solid m.p. 245°-250° C.

δ(CDCl$_3$): 6.78 (1H, d J=5.5 Hz), 7.0-7.25 (2H, m), 7.45,7.5 (1H, dd, J=5 Hz), 8.05 (1H, s), 8.25 (1H, d, J=5.5 Hz).

Found: C,55.87; H,3.72; N,26.20.

$C_{10}H_8N_4S$ requires: C,55.57; H,3.70; N,25.92%.

PHARMACOLOGICAL DATA

Mouse Oxazolone Screen

Compounds were tested for topical anti-inflammatory activity in a screen using the mouse sensitized to oxazolone, by a method modified from that of Dietrich and Hess [Int. Arch. Allergy, 38, 246 (1970)].

Mice were sensitized with oxazolone (2 mg in 20 $\mu$l EtOH) on a shaved area of the abdomen. 5 days later, the animals received 10 $\mu$l THF/MeOH (1:1 v/v) on the right ear and the test compound in the same solvent on the left ear. 1 hour later, the animals were challenged with 100 $\mu$g oxazolone in 10 $\mu$l acetone on each ear. Ear weights were measured 24 hours later. Percentage inhibition of the inflammatory swelling refers to the increase in weight of left ears (oxazolone plus compound in THF/MeOH) compared to untreated negative controls, as a proportion of the increase in weight of right ears (oxazolone plus THF/MeOH only) over similar controls.

In this test the compound of Example 2 caused an inhibition of 43% at a dose of 200 $\mu$g/ear ($p<0.01$ in students 't'-test).

Mouse Cantharidin Screen

Compounds were tested for topical anti-inflammatory activity in a cantharidin mouse ear screen, modified from Swingle, Reiter and Schwartzmiller [Arch. Int. Pharmacodyn. 254, 168–176, 1981].

25 $\mu$g cantharidin (in 10 $\mu$l THF-MeOH 1:1 v/v) was applied to both ears. Compound, in the same solvent, was applied at the same time, to the left ear only. Ears were weighed after 24 hours. Percentage inhibition of the acute inflammatory swelling refers to the increase in weight of left ears (cantharidin plus compound) compared to solvent-treated negative controls, as a proportion of the increase in weight of right ears (cantharidin alone) over similar controls.

The compound of Example 4 gave an inhibition of 42% at a dose of 200 $\mu$g/ear ($p<0.01$ in student's 't'-test).

We claim:

1. A compound of the formula (I) or a pharmaceutically acceptable salt or solvate thereof:

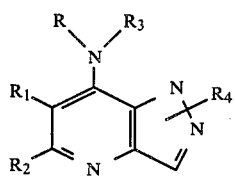

wherein:

R is hydrogen or $C_{1-6}$ alkyl;

$R_1$ and $R_2$ are both hydrogen; or $R_1$ is hydrogen, phenyl or $C_{1-6}$ alkyl; and $R_2$ is CN, $CR_5R_6Y$ where $R_5$ and $R_6$ are independently selected from hydrogen and $C_{1-4}$ alkyl and Y is selected from hydrogen, or $OR_7$ or $SR_7$ where $R_7$ is hydrogen, $C_{1-4}$ alkyl or $C_{2-4}$ alkanoyl, and Y is also $NR_8R_9$ where $R_8$ and $R_9$ are independently hydrogen, $C_{1-4}$ alkyl, $C_{2-4}$ alkenyl or $C_{2-4}$ alkanoyl or together are $C_{4-6}$ polymethylene, or $COR_{10}$ where $R_{10}$ is OH, $C_{1-4}$ alkyl, $C_{1-6}$ alkoxy, $C_{2-6}$ alkenyloxy, phenoxy or benzyloxy wherein the phenyl/benzyl moiety is optionally substituted by one or two of halogen, $CF_3$, $C_{1-4}$ alkoxy and $C_{1-4}$ alkyl; or $R_{10}$ is $NR_{16}R_{17}$ wherein $R_{16}$ and $R_{17}$ are independently hydrogen, $C_{2-6}$ alkyl, $C_{2-6}$ alkenyl, benzyl or phenyl optionally substituted as described above; or $R_2$ is hydrogen, $C_{1-6}$ alkyl, or phenyl optionally substituted by halogen, $CF_3$, $C_{1-4}$ alkoxy or $C_{1-4}$ alkyl; and $R_1$ is CN, $CR_5R_6Y$ or $COR_{10}$ as defined for $R_2$ above; or $R_1$ and $R_2$ together form $C_3-C_6$ polymethylene optionally substituted by $C_1-C_4$ alkyl;

$R_3$ is selected from furyl, thienyl, pyrryl, benzofuranyl, benzothienyl, and indolyl optionally substituted by one or two substituents selected from halogen, $CF_3$, $C_{1-4}$ alkoxy, $C_{1-4}$ alkyl, hydroxy, nitro, cyano, $C_{2-10}$ acyloxy, $NR_{11}R_{12}$ wherein $R_{11}$ and $R_{12}$ are independently selected from hydrogen, $C_{1-6}$ alkyl, $C_{2-7}$ alkanoyl or $C_{1-6}$ alkylsulphonyl; or $COR_{13}$ wherein $R_{13}$ is hydroxy, $C_{1-6}$ alkoxy or $NR_{14}R_{15}$ wherein $R_{15}$ and $R_{14}$ are independently selected from hydrogen or $C_{1-6}$ alkyl; and $R_4$ is hydrogen, or $C_{1-4}$ alkyl, or benzyl optionally substituted in the phenyl ring by one or more of halogen, $CF_3$, $C_{1-4}$ alkyl, and is attached at nitrogen atom 1 or 2.

2. A compound according to claim 1 in which R is selected from hydrogen, methyl, ethyl, n- and iso-propyl.

3. A compound according to claim 1 in which $R_1$ and $R_2$ are independently selected from hydrogen, methyl, ethyl, n- and iso-propyl and phenyl, aminomethyl optionally N- substituted and acetamidomethyl, or $R_1$ and $R_2$ together may be $C_{3-4}$ polymethylene.

4. A compound according to claim 1 in which $R_4$ is selected from hydrogen, methyl, ethyl, n- and iso-propyl and benzyl.

5. A compound selected from the group consisting of:
ethyl 7-thienylamino-1H-pyrazolo[4,3-b]pyridine-6-carboxylate;
7-Thienylamino-1H-pyrazolo[4,3-b]pyridine;
ethyl 7-(3-thienylamino)-1H-pyrazolo[4,3-b]pyridine-6-carboxylate; and
7-(3-Thienylamino)-1H-pyrazolo[4,3-b]pyridine; and pharmaceutically acceptable salts and solvates thereof.

6. A pharmaceutical composition for treatment of inflammatory or allergic disorders which comprises an effective amount of a compound of formula (I) as claimed in claim 1 or a pharmaceutically acceptable salt or solvate thereof and a pharmaceutically acceptable carrier.

7. A method of treatment or prophylaxis of inflammatory and/or allergic conditions in mammals including man which comprises the administration of an effective amount of a compound of formula (I) as claimed in claim 1 or a pharmaceutically acceptable salt or solvate thereof to the sufferer.

8. A compound according to claim 1 in which $R_3$ is selected from furyl, thienyl, pyrryl, benzofuranyl, benzothienyl and indolyl optionally substituted by one or two chloro, bromo, methoxy, ethoxy, n- and iso-propoxy, methyl, ethyl, n- and iso-propyl, n-, iso-, sec- and tert-butyl, hydroxy, nitro, cyano, acetoxy, propionyloxy, benzyloxy, $NR_{11}{}^1R_{12}{}^1$ wherein $R_{11}{}^1$ and $R_{12}{}^1$ are independently selected from hydrogen, methyl, ethyl, n- and iso-propyl; acetyl, propionyl, methylsulphonyl and ethylsulphonyl; $COR_{13}{}^1$ wherein $R_{13}{}^1$ is hydroxy, methoxy, ethoxy or $NR_{14}{}^1R_{15}{}^1$ wherein $R_{14}{}^1$ and $R_{15}{}^1$ are independently selected from hydrogen, methyl, n- and iso-propyl.

* * * * *